US007863491B1

(12) United States Patent
Bonso

(10) Patent No.: US 7,863,491 B1
(45) Date of Patent: Jan. 4, 2011

(54) METHOD FOR THE PRODUCTION OF GAS CLATHRATES

(75) Inventor: Bernd Bonso, Berlin (DE)

(73) Assignee: Reto Mebes, Hombrechtikon (CH)

( * ) Notice: Subject to any disclaimer, the term of this patent is extended or adjusted under 35 U.S.C. 154(b) by 536 days.

(21) Appl. No.: 11/666,745

(22) PCT Filed: Oct. 28, 2005

(86) PCT No.: PCT/EP2005/011576

§ 371 (c)(1), (2), (4) Date: Apr. 24, 2008

(87) PCT Pub. No.: WO2006/048197

PCT Pub. Date: May 11, 2006

(30) Foreign Application Priority Data

Nov. 1, 2004 (DE) ........................ 10 2004 053 627

(51) Int. Cl.
*C07C 9/00* (2006.01)

(52) U.S. Cl. ........................................................ 585/15

(58) Field of Classification Search .................... 585/15
See application file for complete search history.

(56) References Cited

U.S. PATENT DOCUMENTS

| | | | | |
|---|---|---|---|---|
| 4,920,752 A * | 5/1990 | Ehrsam | 62/46.1 |
| 5,473,904 A * | 12/1995 | Guo et al. | 62/46.1 |
| 5,536,893 A * | 7/1996 | Gudmundsson | 585/15 |
| 6,028,234 A * | 2/2000 | Heinemann et al. | 585/15 |
| 6,082,118 A * | 7/2000 | Endrizzi et al. | 62/46.1 |
| 6,180,843 B1 * | 1/2001 | Heinemann et al. | 585/15 |
| 6,653,516 B1 * | 11/2003 | Yoshikawa et al. | 585/15 |
| 2002/0083720 A1 * | 7/2002 | Takao et al. | 62/54.1 |
| 2005/0059846 A1 * | 3/2005 | Kohda et al. | 585/15 |
| 2006/0009664 A1 * | 1/2006 | Lokshin et al. | 585/15 |

FOREIGN PATENT DOCUMENTS

EP 1 329 253 B1 7/2003

* cited by examiner

*Primary Examiner*—Ellen M McAvoy
(74) *Attorney, Agent, or Firm*—Jonathan Myers

(57) ABSTRACT

A method is disclosed for continuously producing gas clathrates, comprising: introducing a reaction gas and a reaction liquid both required for clathrate formation into a reaction chamber; adjusting in the reaction chamber the conditions such that clathrates form; adjusting the conditions in an outlet port of the reaction chamber such that ice-containing clathrates form in the outlet port of the reaction chamber, and arranging a cooling device in the outlet port and within the outlet port, to block the outlet port on the reaction chamber side; comminuting the ice-containing clathrates into ice chips using a comminutor, downstream from the cooling device and upstream from a transport line connected to the outlet port for removing the ice chips from the transport line side of the outlet port; and transporting the ice chips containing clathrates away via the transport line connected to the outlet port.

9 Claims, 1 Drawing Sheet

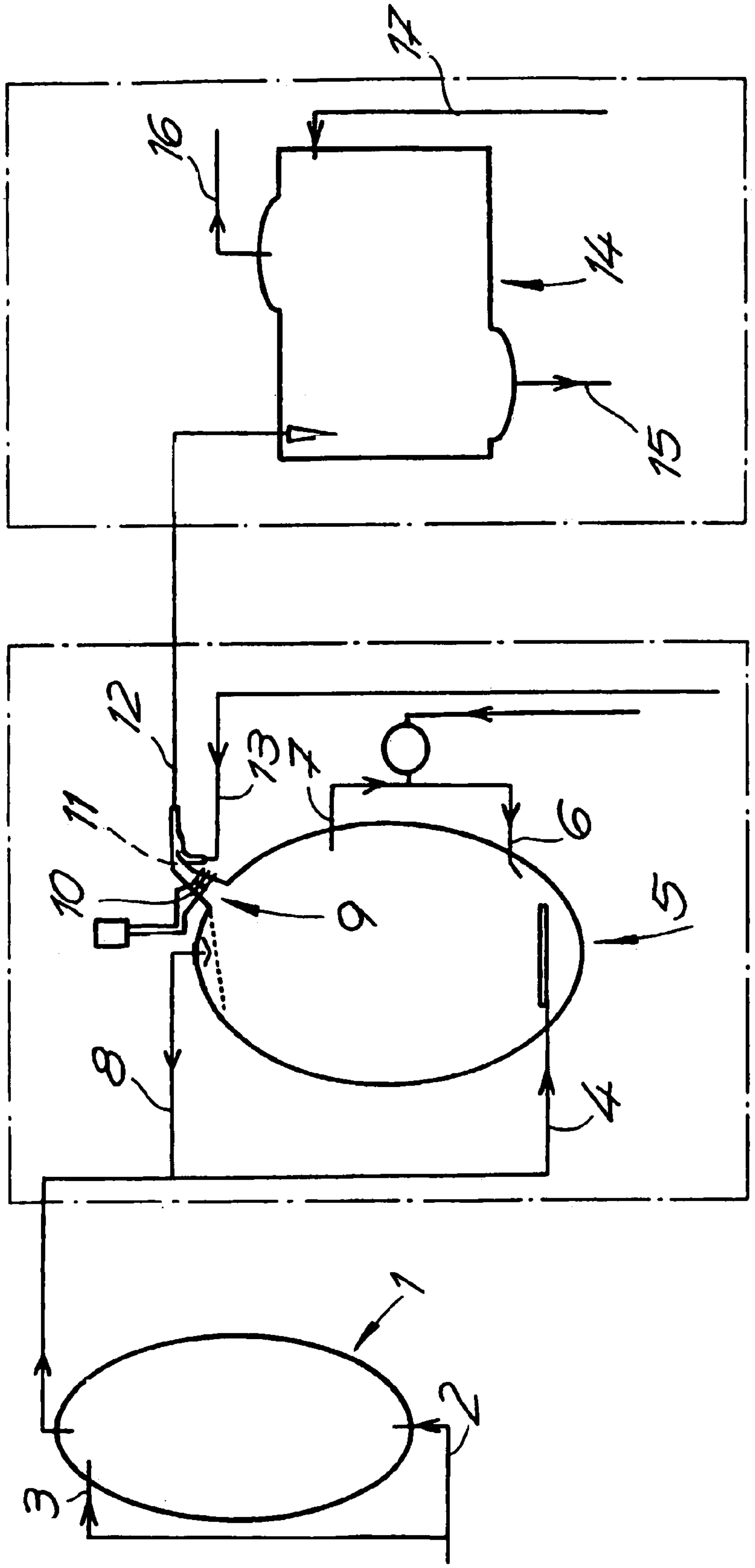
1
2
3
4
5
6
7
8
9
10
11
12
13
14
15
16
17

METHOD FOR THE PRODUCTION OF GAS CLATHRATES

CROSS REFERENCE TO RELATED APPLICATIONS

This application is the US national phase of PCT application PCT/EP2005/011576, filed 28 Oct. 2005, published 11 May 2006 as WO 2006/048197, and claiming the priority of German patent application 102004053627.9 itself filed 1 Nov. 2004, whose entire disclosures are herewith incorporated by reference.

The invention relates to a method of producing gas clathrates, where at least one reaction gas that is required for clathrate formation and at least one reaction liquid that is required for clathrate formation are introduced into a reaction chamber and in the reaction chamber the conditions are adjusted such that clathrates form from the reaction gas and the reaction liquid.

The production of gas clathrates or gas hydrates is fundamentally known. In particular gases that contain hydrocarbons, for instance methane or even hydrogen, are bonded in the form of clathrates or hydrates. In this manner the gases can be stored in a less voluminous and relatively easily manageable manner. The gases, for instance natural gas, can be stored in this manner above all as energy carriers and, in comparison to the free gaseous state, can be transported simply and with no problems.

Methods of producing gas clathrates of the type described above are fundamentally known in practice. However, as a rule these methods and the associated apparatus are very complex and leave a great deal to be desired in terms of their effectiveness and in terms of the clathrate yield. Above all the production speed for clathrates is frequently unsatisfactorily slow in the known methods. Many of the known methods can only be performed in batches so that for this reason as well the clathrate yield per unit of time leaves much to be desired.

Given this, the underlying object of the invention is to provide a method of the type cited above with which clathrates can be produced in an effective and less complex manner with a high yield and with high production speed. The underlying object of the invention is primarily also to provide a method that can be performed continuously.

For attaining this object, the invention teaches a method of producing gas clathrates, where at least one reaction gas that is required for clathrate formation and at least one reaction liquid that is required for clathrate formation are introduced into a reaction chamber, in the reaction chamber the conditions are adjusted such that clathrates form from the reaction gas and the reaction liquid, furthermore the conditions in the reaction chamber are is adjusted such that ice-containing clathrates forms in an outlet port of the reaction chamber and block the outlet port inside the reaction chamber;

the ice-containing clathrates is comminuted into ice chips using at least one comminutor and the ice chips containing clathrates are transported away via a transport line connected to the outlet port.

Preferably gas clathrates of gases containing hydrocarbons (for instance methane) or of hydrogen as a reaction gas are formed with the inventive method. Within the scope of the invention, particularly preferred is the production of gas hydrates for the production of which water is used as the reaction liquid. Above all, it is also within the scope of the invention that gas clathrates or gas hydrates are formed from natural gases.

In accordance with one highly preferred embodiment, the inventive method is performed continuously, which means that reaction gas and/or reaction liquid is continuously supplied to the reaction chamber and that ice chips containing clathrates are produced and transported away continuously. However, it is not absolutely necessary to perform the inventive method continuously. In accordance with one embodiment of the invention, the method can also be performed with periodic supply of reaction gas and/or reaction liquid and/or with periodically transporting ice chips containing clathrates away. Within the scope of the invention, ice chips containing clathrates means in particular ice chips that completely comprise the gas clathrate or that at least largely comprise the gas clathrate.

One particularly preferred embodiment of the inventive method is characterized in that the reaction gas used for the clathrate formation is purified and compressed prior to being introduced into the reaction chamber. This procedure has proved itself in particular for continuous clathrate production. Such simultaneous purification and compression of a reaction gas is disclosed in EP 1 329 253 A1. Within the scope of the invention, work is preferably conducted in accordance with that patent. Usefully, the purification and compression of the reaction gas is performed in at least one purification/compression chamber in that a purification liquid is added to the purification/compression chamber that is filled with the reaction gas such that the reaction gas is purified and such that the reaction gas is compressed due to the purification/compression chamber being filled. Within the scope of these inventive measures, it is useful that purification and compression of the reaction gas occurs simultaneously in a single purification/compression chamber. It is within the scope of the invention to combine or successively switch a plurality of such chambers. Preferably work is performed as follows during the purification and compression of the reaction gas: The reaction gas is initially usefully introduced, preferably from below, into the purification/compression chamber that is filled with the purification liquid. During this procedure, preferably care is taken that the reaction gas, when added to the purification liquid, has the smallest possible bubbles so that the contact surface is large. In this manner the reaction gas is purified using the purification liquid. The purification liquid is displaced out of the purification/compression chamber and for instance transferred to a reservoir. In a second step, the purification liquid is then introduced, specifically is injected or sprayed, into the purification/compression chamber that is filled with the reaction gas, for which purpose a corresponding spray head or a corresponding spray nozzle is provided in the upper area of the purification/compression chamber. This results in an effective final purification of the reaction gas and at the same time the purification/compression chamber is filled with the purification liquid so that the reaction gas is compressed.

Within the scope of the purification described above, it is useful that a purification liquid is used that takes up only small quantities of the reaction gas to be purified under the conditions in the purification/compression chamber. The purification liquid can be for instance a glycol that in particular takes up only small quantities of methane under the above-described conditions. On the other hand, the purification liquid is selected such that it easily takes up other impurities in the reaction gas, for instance carbon dioxide or water.

The reaction gas that has preferably been purified and compressed in the manner described above is then introduced under pressure into the reaction chamber that is at least partially filled with the reaction liquid. It is usefully introduced via an appropriate valve. It is within the scope of the invention that the reaction gas is introduced into the reaction chamber at the same pressure as in the purification/compression chamber. Care is is preferably also taken during the introduction into the reaction chamber that the reaction gas enters the reaction liquid with the smallest possible bubbles so that the contact surface is as large as possible. In accordance with one embodiment, at least one mixing device is provided in the reaction chamber for effective mixing of reaction liquid and reaction gas.

In accordance with the invention, the conditions in the reaction chamber are set such that clathrates form. Setting the conditions means in particular setting the pressure and/or temperature and/or concentration of the reaction partners.

For setting the conditions in the reaction chamber it is furthermore within the scope of the invention that the reaction liquid is continuously or periodically introduced into the reaction chamber and/or removed from the reaction chamber. In particular the required pressure for clathrate formation is set using the reaction liquid. When gas hydrates are produced, the reaction liquid is water. Thus for instance water is used for producing methane hydrate as the reaction liquid. For effective clathrate formation, it is within the scope of the invention that the density and/or the adsorbability and/or the absorbability of the reaction liquid is influenced or controlled by adding salts.

It is within the scope of the invention that the formation of the ice-containing clathrates is brought about or promoted by setting the conditions, in particular by setting the pressure and/or temperature in the reaction chamber. The clathrate can then collect in the outlet port in the form of ice based on its density. In accordance with one particularly preferred embodiment of the invention, ice-containing clathrates is formed with at least one cooling device arranged in the outlet port or ice-containing clathrates is promoted in the outlet port with this at least one cooling device. For forming the ice-containing clathrates, in accordance with one preferred embodiment of the invention both measures are used, that is, a cooling device and setting the conditions. As already described above, the ice-containing clathrates preferably totally or essentially comprises the gas clathrate. It is furthermore within the scope of the invention that, under the pressure prevailing in the reaction chamber, the ice-containing clathrates is pressed into a mass of ice in the outlet port. The embodiment of the ice mass contributes in a particularly effective manner to solving the problem in accordance with the invention. The conditions in the reaction chamber that are required for forming the clathrates, that is in particular pressure and/or temperature, can be maintained in a simple and effective manner using the ice mass.

The outlet port is usefully formed by at least one outlet pipe attached to the reaction chamber. It is within the scope of the invention that the outlet port or the outlet pipe is arranged in the upper part or at the head of the reaction chamber.

Usefully the ice or the ice mass is comminuted with the at least one comminutor in the transport line area of the outlet port. The comminutor can be active, that is, it can be a comminutor that is driven by a motor or the like. However, the comminutor can also be passive, that is, a comminutor that is not driven, that comprises cutters for instance. It is also possible to combine active and passive comminutor. In accordance with one very preferred embodiment of the inventive method, a transport liquid is supplied that transports the transportable or pumpable ice chips through the transport line. This transport liquid is usefully supplied in the area facing away from the reaction chamber or on the side of the transport line of the outlet side and/or at the beginning of the transport line. According to one inventive embodiment, the transport liquid can comprise, at least in part, the reaction liquid. If water for instance is used for the reaction liquid for gas hydrate formation, the transport liquid can also comprise water, at least in part or completely. It is also within the scope of the invention that at least a part of the transport liquid comprises a liquid for energy production, in particular a liquid fuel, for instance benzene. Then both the gas stored in the clathrates and the transport liquid can be used for energy production. Thus for instance benzene as the transport liquid can be added to methane clathrate and both the methane stored in the clathrate and the benzene can be used for energy production and for instance supplied to an appropriate motor. Thus, by selecting a special transport liquid, it is possible to simultaneously store the gas in the clathrate and to store a liquid fuel, for instance for motor vehicles. The transport line usefully has at least one pump for conveying the ice chips or the transport liquid.

It is within the scope of the invention that the transport liquid is added, with the ice chips it carries, to a transport and/or storage chamber and that at least a portion of the transport liquid is removed from this transport and/or storage chamber. Advantageous chamber volume utilization for the gas clathrates is attained by removing the transport liquid that has been introduced into the chamber. Usefully, transport liquid with ice chips is added to the chamber and simultaneously excess transport liquid is removed from the transport and/or storage chamber.

It is furthermore within the scope of the invention that at least a portion of the transport liquid removed from the transport and/or storage chamber is returned for transporting the ice chips through the transport line. Thus the transport liquid goes is recirculated. For this, the transport liquid drawn from the transport and/or storage chamber is usefully filtered so that it is free of clathrates.

The invention is based on the recognition that very effective and at the same time uncomplicated production of gas clathrates or gas hydrates is possible using the inventive method. It should in particular be stressed that the inventive method permits an advantageously high clathrate yield and is characterized in particular by high production speed for gas clathrates. It should also be emphasized that the inventive method can advantageously be performed continuously and that in particular during continuous operations a very high production speed with a high clathrate yield is possible. It should also be noted that the inventive method or an apparatus for the inventive method works in a manner that is very functionally secure and free of interruptions. Such an apparatus can also be created in a relatively simple, uncomplicated, and cost-effective manner.

The invention will be explained in greater detail in the following using a drawing depicting only one illustrated embodiment. The single FIGURE is a schematic depiction of an inventive apparatus for performing the inventive method.

The FIGURE initially depicts a purification/compression chamber 1 for simultaneously cleaning and compressing a reaction gas. The reaction gas can be a gas containing carbon dioxide, for instance methane. The purification/compression chamber is initially filled with a purification liquid, for instance with a glycol. The reaction gas is then added from below to the purification/compression chamber via a supply line 2. Advantageously, care is taken that the reaction gas is conducted through the purification liquid with the smallest possible bubbles so that the greatest possible contact surface results. In this manner the reaction gas is purified using the purification liquid. The purification liquid is transported out of the purification/compression chamber in a manner not shown in greater detail. Then the purification/compression chamber 1 is filled with the reaction gas. Then purification liquid is re-added to the purification/compression chamber 1 via the supply line 3; it is usefully injected in from above. In this manner the reaction gas is further purified with the purification liquid. The reaction gas is compressed by filling the purification/compression chamber with the purification liquid.

The reaction gas precompressed or compressed in this manner is then fed out of the purification/compression chamber 1 via a feed line 4 under the pre-pressure into a reaction chamber 5 that is filled with reaction liquid. The reaction gas is introduced through the reaction liquid from below. Usefully, care is taken here as well that the reaction gas fed in enters the reaction liquid with small bubbles in order to assure the greatest possible contact surface. In the reaction chamber 5, the conditions, that is, in particular the pressure and the temperature, are adjusted such that a gas clathrate forms from the reaction gas and the reaction liquid. Additional reaction liquid is added to the reaction chamber 5 via an input line 6. When needed, excess reaction liquid can be removed from the reaction chamber 5 via an evacuation line 7. When needed, excess reaction gas can be removed from the reaction chamber 5 via a discharge line 8. In accordance with one particularly preferred embodiment of the invention, reaction gas is continuously supplied through the feed line 4 and reaction liquid is continuously supplied through the input line 6 and the gas clathrate formed is also usefully continuously removed from the reaction chamber 5.

An outlet port 9 is provided in the upper area of the reaction chamber 5 for removing the gas clathrate formed. In the illustrated embodiment in accordance with the FIGURE, a cooling device 10 is connected to this outlet port 9, and it can produce ice-containing clathrates in the area of the outlet port 9. This ice-containing clathrates forms an ice mass that preferably blocks the outlet port 9 during the formation of the clathrates in the reaction chamber 5. The ice mass is also forced under the pressure in the reaction chamber 5 into the outlet port 9. Because the outlet port 9 is blocked by the ice mass, the conditions in the reaction chamber 5, in particular the pressure in the reaction chamber 5, can be adjusted very precisely, and in this manner effective clathrate formation with high yield is attained.

Usefully arranged in the outlet direction downstream of the cooling device 10 of the outlet port 9 is a comminutor 11, not shown in greater detail in the FIGURE, with which the ice-containing clathrates, downstream of the cooling device 10 and upstream of a transport line 12 and/or in the front area of the transport line 12, is comminuted into transportable ice chips. The transportable ice chips are then conveyed away via the transport line 12.

For conveying the transportable ice chips, a transport liquid is preferably supplied via a supply line 13. The transport liquid is usefully supplied in the transport line area of the outlet port 9 and/or in the initial area of the transport line 12. In the illustrated embodiment in accordance with the FIGURE, the transport liquid is supplied in the transport line area of the outlet port 9. The ice chips can then be transported away through the transport line 12 with no problem using the transport liquid. It is within the scope of the invention that the ice chips are continuously transported away with the transport liquid.

The ice chips are then supplied via the transport line 12 to a transport and/or storage chamber 14 using the transport liquid. The transport liquid available in the transport and/or storage chamber 14 can be simultaneously removed via the evacuation line 15 and preferably returned completely to the supply line 13. Evacuating the transport liquid from the transport and/or storage chamber 14 results in quite volume-saving storage of the gas clathrate in the transport and/or storage chamber 14. If in the framework of the inventive method here methane hydrate is produced and water is used for the transport liquid, the methane hydrate can float in the water in the transport and/or storage chamber, and the water, as transport liquid, can be removed in a simple manner via the evacuation line 15.

In addition, it should be noted that transporting an inventively produced gas clathrate using the transport liquid is much safer than transporting the gas under pressure in conventional lines. Significantly larger quantities of the gas stored in the form of gas clathrates can be conducted in the same period of time through the same conduits.

The gas clathrate received in the transport and/or storage chamber 14 can in particular be converted back to gas by heating and this gas can then be removed from the transport and/or storage chamber via the discharge line 16 and sent to its application. Transport liquid can be added via the feed line 17 to the transport and/or storage chamber 14 in order in particular to set the output pressure of the resultant gas. In addition, adding transport liquid via the feed line 17 can prevent undesired gases from penetrating into the transport and/or storage chamber 14.

As already indicated above, in particular a liquid can be used for the transport liquid that can be used to produce energy. In accordance with one embodiment, the gas clathrate is transported with a liquid fuel for the transport liquid or is introduced into the transport and/or storage chamber 14. Thus for example methane clathrate can be transported with benzene as the vehicle liquid. In the transport and/or storage chamber 14 then initially the methane can be developed, for instance by heating, and in particular can be used or consumed in a motor. Then the transport liquid benzene can be supplied from the transport and/or storage chamber 14 to the motor for use or consumption. It is possible to store gas and liquid fuel in the transport and/or storage chamber 14 simultaneously using this inventive method variant. In this context, it is also within the scope of the invention to transport or to introduce to the transport and/or storage chamber 14 a hydrogen clathrate with liquefied natural gas for the transport liquid. In this embodiment, energy can be produced both from the hydrogen stored as clathrate and from the natural gas.

Above it was indicated that the stored gas is usefully released from the gas clathrate by heating the gas clathrate or the gas clathrate/transport liquid mixture. Heating then occurs preferably via the transport liquid, whereby an appropriate heat source can be provided in the transport liquid and/or outside on the wall of the transport and/or storage chamber 14.

The invention claimed is:

1. A method of continuously producing gas clathrates, the method comprising the steps of:

introducing at least one reaction gas required for clathrate formation and at least one reaction liquid required for clathrate formation into a reaction chamber;

adjusting in the reaction chamber the conditions such that clathrates form;

adjusting the conditions in an outlet port of the reaction chamber such that ice-containing clathrates form in the outlet port of the reaction chamber, and arranging at least one cooling device in the outlet port and within the outlet port, to block the outlet port on the reaction chamber side;

comminuting the ice-containing clathrates into ice chips using at least one comminutor, wherein the comminuting takes place downstream from the at least one cooling device and upstream from a transport line connected to the outlet port for removing the ice chips from the transport line side of the outlet port; and transporting the ice chips containing clathrates away via the transport line connected to the outlet port.

2. The method in accordance with claim 1, further comprising the step of purifying and compressing the reaction gas used for the clathrate formation before introduction into the reaction chamber.

3. The method in accordance with claim 2 wherein the purification and compression of the reaction gas is performed in at least one purification/compression chamber by adding a purification liquid to the purification/compression chamber after filling the purification/compression chamber with the reaction gas such that the reaction gas is purified and such that the reaction gas is compressed by the filling of the purification/compression chamber.

4. The method in accordance with claim 2 wherein the purified and compressed reaction gas is introduced under pressure into the reaction chamber after at least partially filling same with the reaction liquid.

5. The method in accordance with claim 1 wherein setting the conditions in the reaction chamber is carried out by introducing the reaction liquid into or removing it from the reaction chamber.

6. The method in accordance with claim 1 wherein a transport liquid is used to transport the ice chips through the transport line.

7. The method in accordance with claim 6 wherein the transport liquid is at least in part the reaction liquid.

8. The method in accordance with claim 1, further comprising the steps of:

adding the transport liquid with the ice chips, to a transport and/or storage chamber and removing at least a portion of the transport liquid from the transport and/or storage chamber.

9. The method in accordance with claim 8, further comprising the step of:

recirculating the portion of the transport liquid removed from the transport and/or storage chamber for transporting the ice chips through the transport line.

* * * * *